United States Patent
Iezzi et al.

(10) Patent No.: US 6,841,712 B1
(45) Date of Patent: Jan. 11, 2005

(54) PROCESS FOR THE DEHYDROGENATION OF ETHYLBENZENE TO STYRENE

(75) Inventors: Rodolfo Iezzi, Milan (IT); Domenico Sanfilippo, Milan (IT)

(73) Assignee: Snamprogetti S.p.A., San Donato Milanese (IT)

(*) Notice: Subject to any disclaimer, the term of this patent is extended or adjusted under 35 U.S.C. 154(b) by 313 days.

(21) Appl. No.: 10/070,440

(22) PCT Filed: Sep. 19, 2000

(86) PCT No.: PCT/EP00/09196

§ 371 (c)(1),
(2), (4) Date: Mar. 19, 2002

(87) PCT Pub. No.: WO01/23336

PCT Pub. Date: Apr. 5, 2001

(30) Foreign Application Priority Data

Sep. 30, 1999 (IT) ........................................ MI99A2031

(51) Int. Cl.[7] ........................ C07C 5/327; C07C 5/333; C07C 5/32

(52) U.S. Cl. ........................ 585/444; 585/445; 585/440; 585/660; 585/661

(58) Field of Search ................................. 585/444, 445, 585/440, 660, 661

(56) References Cited

U.S. PATENT DOCUMENTS 3,472,794 A 10/1969 Carter et al.
6,242,660 B1 6/2001 Buonomo et al.

FOREIGN PATENT DOCUMENTS

| AU | 499 659 | 4/1997 |
|---|---|---|
| EP | 0 794 004 | 9/1997 |
| EP | 0 905 112 | 3/1999 |

*Primary Examiner*—Thuan D Dang
(74) *Attorney, Agent, or Firm*—Oblon, Spivak, McClelland, Maier & Neustadt, P.C.

(57) ABSTRACT

A process is described for the dehydrogenation of ethylbenzene to styrene in a fluid-bed reactor-regenerator system, which uses a catalyst based on iron oxide supported on a modified alumina and promoted with further metal oxides.

18 Claims, 1 Drawing Sheet

PROCESS FOR THE DEHYDROGENATION OF ETHYLBENZENE TO STYRENE

Figure 1:
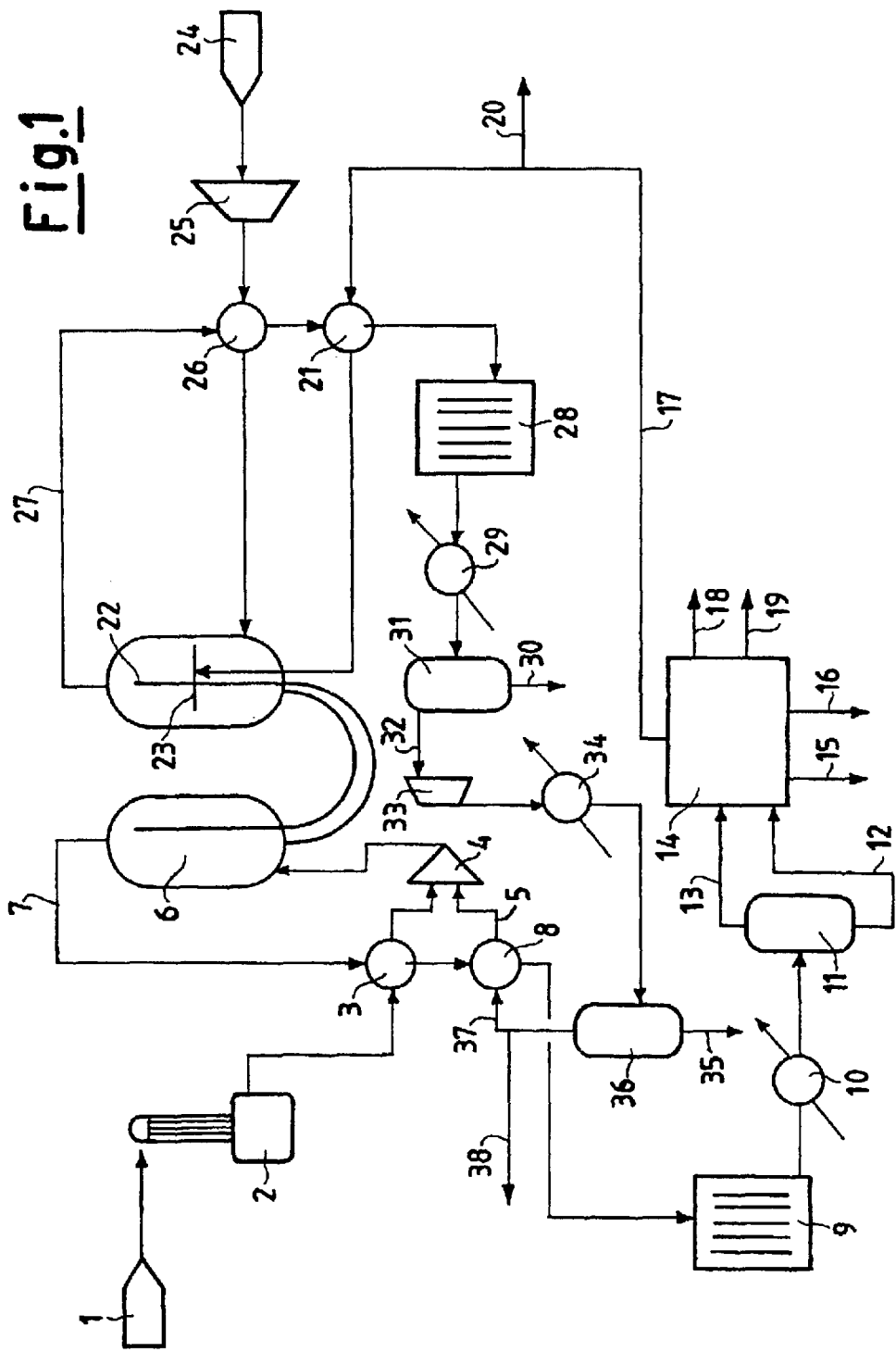

The present invention relates to a process for the dehydrogenation of ethylbenzene to styrene in a fluid-bed reactor/regenerator system, in the presence of a catalyst based on an iron oxide and further promoters, selected, e.g., from metal oxides such as alkaline oxides, earth-alkaline metal oxides and/or oxides of the metals of the group of lanthanides, supported on a modified alumina.

Styrene is an important intermediate which can be used in the preparation of plastic materials and rubbers.

More specifically, styrene is used for the production of polystyrenes (GPPS crystals, high impact HIPS and expandable EPS), acrylonitrile-styrene-butadiene (ABS) and styrene-acrylonitrile (SAN) copolymers and styrene-butadiene rubbers (SBR).

The dehydrogenation reaction of ethylbenzene to styrene has a few particular characteristics which should be taken in account for the technological design.

The first lies in the fact that the reaction is controlled by thermodynamic equilibrium and consequently the conversion per passage is not total. The dehydrogenation degree increases with a rise in the temperature and with a decrease in the total pressure, the reaction taking place at a constant pressure, with an increase in the volume. In order to obtain economically acceptable conversions, it is therefore necessary to carry out the reaction at temperatures generally ranging from 540 to 630° C.

The use of high temperatures however stimulates side reactions characterized by a greater activation energy with respect to the dehydrogenation value. As a result of this, more or less significant quantities of by-products mainly consisting of toluene, benzene, coke and light products are formed together with the main product.

It is therefore necessary to use a catalyst capable of directing the reaction towards the desired product.

The last important aspect consists in the fact that the reaction is extremely endothermic, with a reaction heat equal to 28 Kcal/moles of styrene corresponding to 270 Kcal/kg of styrene produced.

The high heat required and the high thermal levels at which it must be exchanged greatly influence the technological design.

The technologies at present commercialized (Fina/Badger and Lummus/UOP Classic SM processes) satisfy the demands imposed by the thermodynamics of the reaction by means of processes which use a bulk catalyst prevalently based on iron, oxide and promoted with alkalis, and which comprise the use of:

several adiabatic reactors in series, with intermediate heating steps at a temperature ranging from 540° C. to 630° C. and with contact times in the order of tenths of a second;

radial flow reactor which operate under vacuum at a pressure ranging from 30.39 to 50.65 Kpa (absolute Pascal) (0.3 to 0.5 ata) (absolute atmospheres); and water vapor which is fed with the charge to be dehydrogenated.

Water is the main component in the charge fed to the reactor. The typical molar concentration is 90%, even if higher concentrations are often adopted to lengthen the chemical life of the catalyst.

The vapor has the function of:

reducing the partial pressure of the products and therefore favorably shifting the thermodynamic equilibrium;

contributing to the removal of the coke which is deposited on the surface of the catalyst, there being no regeneration of the catalyst with air;

supplying the heat necessary for the dehydrogenation of the ethylbenzene;

slowing down the aging of the catalyst.

Operating with these technologies, conversions ranging from 60 to 65% are obtained, with a selectivity to styrene higher than 90% by weight.

These processes however have the following disadvantages:

use of large quantities of vapor ($H_2O$/EB=9.0–10 molar) superheated with temperatures higher than 700° C.; this impels the use of superheating ovens and therefore high investment costs;

aging of the catalyst and consequently the necessity of substituting it after 18–36 months of operation; this involves stopping the unit and consequently interrupting the production for the period necessary for substituting the catalyst;

non-optimized energy recovery; present technologies, in fact, only comprise the recovery of the sensitive vapor heat and not that of the latent heat;

carrying out the reaction under vacuum (average absolute pressure of 40.52 KPa (abs Pa) (0.4 ata)) and therefore in extremely diluted phase in EB; the partial EB pressure is on an average equal to 4.052 KPa (abs Pa) (0.04 ata).

It has now been found that it is possible to overcome these drawbacks by means of a process which uses a fluid-bed reactor/regenerator system and a catalyst based on iron oxide supported on a microspheroidal alumina modified with silica and further metal oxides as promoters.

The process of the present invention has considerable economic advantages, in particular:

thermal profile of the reactor favorable for the reaction thermodynamics;

the heat is directly transferred to the reaction by the regenerated catalyst, superheating ovens are therefore not required for the thermal exchange and the strong remixing of the fluidized bed prevents the formation of hot spots which would lower the selectivity;

the possibility of recycling the hydrogen;

the plant can be run with great flexibility in terms of actual productive capacity with respect to that projected;

the dehydrogenation reaction and the regeneration take place in physically separated zones; this avoids the mixing of hydrocarbon streams with oxygen streams;

the process is carried out at a pressure which is atmospheric or slightly higher; as a result, there are no air infiltrations from the outside in the reaction zone;

the molar concentration of the inert gas/ethylbenzene in the feeding is much lower with respect to commercial technologies;

it is not necessary to effect any specific treatment for reducing the emissions of gas pollutants; and the possibility of operating without water vapor without there being any chemical deterioration in the catalyst.

Japanese patent application 7-328,439 discloses a process for the dehydrogenation of ethylbenzene in the presence of a catalyst which consists of alumina, carrying a complex of potassium ferrate and possibly rare earth metal oxides, modified by basic metallic oxide addition. Said catalyst shows activity when operated in the presence of water but no data are given in said patent application about the performances of the catalyst in the absence of water, as co-feed of ethylbenzene, nor the effect of ageing is detailed. Surprisingly, it was found that through a partial modification of the alumina carrier by silica it was possible to improve significantly the catalytic performances in dehydrogenation yield, with evident advantages. In the same time, the mechanical resistance of the catalyst itself is improved by silica modification making it more suited to fluid bed operations. Furthermore, the catalyst is also able to operate with nitrogen other than with water.

In accordance with this, the present invention relates to a process for dehydrogenating ethylbenzene to styrene which essentially consists in:
(a) reacting ethylbenzene mixed with an inert product, in a fluid-bed reactor, in the presence of a catalytic system consisting of iron oxide and promoters supported on alumina modified with 0.01–10% by weight of silica and operating at a temperature ranging from 400 to 700° C., at a total pressure of 10.13 to 303.9 KPa (abs Pa) (0.1 to 3 ata) and with a GHSV space velocity ranging from 50 to 10,000 h$^{-1}$ (normal liters of the mixture ethylbenzene and inert gas/h×liter of catalyst); and
(b) regenerating the catalyst in a regenerator by burning the coke deposited on its surface at a temperature exceeding 400° C.

The catalytic system used in the process of the present invention consists of:
(1) 1–60% by weight, preferably 1–20%, of iron oxide;
(2) 0.1–20% by weight, preferably 0.5–10%, of at least one alkaline or alkaline earth metal oxide;
(3) 0–15% by weight, preferably 0,1–7% of a second promoter consisting of at least one rare earth oxide;
(4) the complement to 100 being a carrier consisting of a microspheroidal alumina with a diameter selected from those in delta, theta phase or their mixtures, in theta+alpha phase or delta+theta+alpha phase, modified preferably with 0.08–5% by weight of silica.

The carrier has an average particle diameter and particle density such that the final product can be classified as Group-A according to Geldart (Gas Fluidization Technology, D. Geldart, John Wiley & Sons) and a surface area of less than 150 m$^2$/g (BET).

Alkaline metal preferably used as first promoter in the present invention is potassium. Preferred second promoters belonging to the rare earth metals are cerium, lantanium and praseodymium.

An example of catalyst according to the present invention consists of:
(1) 5–50% by weight of iron oxide;
(2) 0,5–10% by weight of a promoter expressed as oxide;
(3) the complement to 100 being a carrier consisting of a microspheroidal alumina with a diameter ranging from 50 to 70 microns selected from those in delta, theta phase or their mixtures, in theta+alpha phase or delta+theta+alpha phase, modified preferably with 0.08–3% by weight of silica. The process for preparing the catalytic system described above can be essentially carried out by means of the following steps:
  preparation of solutions based on derivatives of the components of the catalytic system;
  dispersion of the solutions on carriers as defined above;
  drying of the solids obtained;
  calcination of the dried solids at a temperature ranging from 500 to 900° C.

The dispersion of the catalyst components on the carrier can be carried out using conventional techniques such as impregnation, ion exchange, vapor deposition or surface adsorption.

The "incipient wetness" impregnation technique is preferably used.

According to a preferred embodiment, the catalyst is prepared by:
(a) addition of an aliquot of the promoters to the carrier;
(b) drying at 100–150° C. and, optionally, calcination of the dried solid at a temperature not exceeding 900° C.;
(c) dispersion of the iron oxide and remaining aliquot of the promoters on the modified carrier (a);
(d) drying at 100–150° C. and calcination of the dried solid at a temperature ranging from 500 to 900° C.

Steps c) and d) can be repeated several times.

Nitrogen, methane, hydrogen or water vapor can be used as the gaseous inert product, in a volumetric ratio inert gas/ethylbenzene ranging from 1 to 6, preferably from 2 to 4. Methane and nitrogen are preferably used.

According to a further embodiment of the process of the present invention, the ethylbenzene can be co-fed to the reactor with a paraffin selected from ethane, propane, isobutane, in order to obtain the contemporaneous dehydrogenation of the co-fed products to give styrene and the corresponding olefins respectively.

In particular when the ethylbenzene is fed with ethane, the process can be carried out as described in U.S. Pat. No. 6,031,143.

According to a further embodiment of the process of the present invention, ethylene can be recycled to an alkylation unit together with a stream of benzene to give ehtylbenzene.

In the reactor-regenerator system, the catalyst circulates continuously, in fluidized state, between the reactor and regenerator, thus allowing the process to be carried out in continuous.

The heat necessary for the reaction is provided by the regenerated catalyst which reaches the reactor at a temperature higher than the average reaction temperature.

The catalyst is maintained in a fluidized state in the reactor by the reagent mixture (inert gas/ethylbenzene), which enters the catalytic bed from below, by means of an appropriate distribution system.

The reacted gas, after passing through a system of cyclones or another powder separation system, leaves the reactor from above. The gas can then be sent to a heat exchanger for the preheating of the feeding and subsequently to the separation section where the styrene produced is recovered, whereas the non-reacted charge is recycled to the dehydrogenation reactor and the reaction by-products (light hydrocarbons and hydrogen) are recovered and used in the regenerator as fuel gas.

The catalyst moves in fluidized state in the reactor, in countercurrent with respect to the gas phase. It enters the catalytic bed from above, through a distributor which disperses it equally on the surface of the bed, and it leaves the reactor from below, passing by gravity into a desorption zone where the moving and desorption of the intraparticle gas take place, nitrogen or methane being introduced from below, so that the moved or desorbed gas re-enters the reactor, thus avoiding losses in reagents or products.

It is preferable to operate in the fluid-bed reactor as follows:
  at a temperature ranging from 450 to 650° C. in relation to the desired reaction; the temperature is maintained within the pre-selected values by regulating the flowrate of the regenerated catalyst;
  at a pressure which is atmospheric or slight higher;
  at a GHSV space velocity ranging from 100 and 1000 h$^{-1}$, preferably from 150 to 300 h$^{-1}$; and
  with a residence time of the catalyst in the fluid bed ranging from 5 to 30 minutes, and in the desorption zone from 0.2 to 10 minutes.

According to an embodiment of the process of the present invention, grids can be horizontally arranged inside the reactor, at a distance of 20 to 200 cm from each other, and with a free area ranging from 10 to 90%, preferably from 20 to 40%. The purpose of the grids is to prevent the gas and catalyst from re-mixing, so that the gas flow inside the reactor resembles a plug-flow. The use of these grids allows maximization of the conversion of ethylbenzene and selectivity to styrene.

The selectivity of the reaction can be further improved by the longitudinal thermal profile which is established along the catalytic bed, with the maximum temperature in the upper part where the regenerated catalyst arrives and the minimum temperature in the lower part. The temperature difference along the bed preferably ranges from 15 to 65° C.

In order to optimize the longitudinal thermal profile, the regenerated catalyst can be distributed at various heights of the catalytic bed.

The fluidized catalyst is subsequently sent to the regenerator through a pneumatic transport system consisting of:
- a transport line with at least one zone in which the catalyst moves downwards by the introduction of suitable quantities of gas at appropriate heights, and
- a zone in which the catalyst moves upwards until it reaches the upper part of the catalytic bed, by the introduction of gas at the base of the raiser.

The regenerator preferably has similar dimensions to those of the reactor to maintain the catalyst for a period sufficient for its regeneration.

The regeneration of the catalyst is carried out by the combustion of coke with air and oxygen, whereas its heating is effected with the use of methane, a fuel gas, or by-products of the dehydrogenation reaction, at a temperature higher than the average reaction temperature.

The movement of the gas and solid takes place in countercurrent also in the regenerator: air enters the bottom of the catalytic bed, whereas the fuel gas is introduced at suitable heights along the bed.

The gas leaving the regenerator, substantially consisting of nitrogen and combustion products, is passed through a system of cyclones, or other system, situated in the upper part of the apparatus, to separate the entrained powders and is then sent to a heat exchanger to preheat the combustion air.

Before being discharged into the atmosphere, these gases can be treated with a filter system or other devices for reducing the powder content to a few tenths of mg per $Nm^3$ of gas.

In the regenerator, it is preferable to operate at atmospheric pressure or slightly higher, at a space velocity ranging from 100 to 1,000 $h^{-1}$ and with a residence time of the catalyst ranging from 5 to 60 minutes, preferably from 20 to 40 minutes.

The regenerated and reheated catalyst is sent to the reactor by means of a pneumatic system having the characteristics described above.

The use of the reactor-regenerator system has the following advantages:
- the possibility of keeping the operating parameters and catalytic performances constant for the whole technical life of the plant;
- the heat is transferred to the reaction directly by the regenerated catalyst; there is therefore no need for super-heating ovens for the thermal exchange and the strong re-mixing of the fluid bed prevents the formation of hot spots which would lower the selectivity;
- the hydrogen can be recycled;
- the process can be carried out in continuous without having to modify the operating parameters during the life of the plant;
- the reaction and regeneration take place in physically separated zones so that the hydrocarbon streams do not mix with streams containing oxygen;
- the molar concentration inert product/ethylbenzene in the feeding is much lower with respect to the commercial technologies.

With reference to FIG. 1, a possible application of the reactor-regenerator scheme is provided, which uses the catalyst based on supported iron oxide.

The liquid stream of ethylbenzene (1), consisting of fresh and recycled feeding, at room temperature and a pressure of 263.38 KPa (abs Pa) (2.6 ata) is vaporized in the evaporator (2), preheated to about 420° C. in the gas-gas exchanger (3), mixed in a suitable mixer (4) with a stream (5) prevalently consisting of nitrogen and whose origin is described hereunder, and fed to the reactor (6) by means of an appropriate distributor situated in the lower part. The stream (7), effluent from the reactor at a temperature of 600° C., at a pressure of 135.76 KPa (abs Pa) (1.34 ata), essentially consisting of nitrogen, styrene, hydrogen and non-reacted ethylbenzene, undergoes a first cooling in the gas-gas exchanger (3) and a second cooling in the gas-gas exchanger (8), from which it flows at a temperature of 320° C. This stream then passes through the filter system (9) to eliminate the fine particles entrained and is subsequently cooled with water to a temperature of 40° C. in the exchanger (10). The mixture becomes biphasic at this temperature as a result of the partial condensation of the hydrocarbon.

The condensed stream (12) is recovered from the bottom in the phase separator (11), and is sent, like the gas stream (13), to the subsequent recovery and purification zone of the products (14), not shown in detail, where the following streams are recovered, using techniques known to experts in the field:
- stream (15) consisting of pure styrene (product);
- stream (16) consisting of ethylbenzene, which is recycled to the dehydrogenation;
- stream (17) essentially consisting of nitrogen and hydrogen, containing light hydrocarbons;
- stream (18) essentially consisting of benzene and toluene;
- stream (19) consisting of heavy hydrocarbon by-products.

The stream (17), after flushing stream (20), is heated in the gas-gas exchanger (21) up to a temperature of 550° C. and fed to the regenerator (22) by means of the distributor (23) situated above the air inlet. The stream of air (24) is compressed in the compressor (25) and preheated to a temperature of 560° C. in the gas-gas exchanger (26), before being fed to the regenerator (22). The stream (27) effluent from the regenerator, prevalently consisting of nitrogen and water vapor is subsequently cooled in the exchangers (21) and (26), passes through the filters (28) to eliminate the fine powders entrained and is cooled in the exchanger (29) at 40° C.

The stream of condensed water (30) is separated in the vessel (31), whereas the remaining gas stream (32), still containing significant quantities of water vapor, is compressed in the compressor (33) at a pressure of 263.38 KPa (abs Pa) (2.6 ata) and is subsequently cooled in the exchanger (34) at such a temperature as to allow the almost complete condensation of the water present. The condensed stream (35) is removed from the bottom of the vessel (36), whereas the gas stream (37), after a part of it has been flushed (38), is heated in the gas-gas exchanger (8). The resulting stream (5) is then treated as described above.

All the catalytic tests are carried out using a quartz micro-reactor in which 50–100 ml of catalyst are charged. The reactor is heated by an electric oven in order to keep the catalytic bed at the desired temperature.

The ethylbenzene is fed to an evaporator by means of a dosing pump and is then mixed with the inert gas whose flow-rate is measured by means of a rotameter.

The reaction mixture is preheated to 200° C. and fed to the reactor from below through a calibrated septum which acts as gas distributor, thus fluidizing the catalyst.

A quartz expansion vase is assembled on the head of the reactor, which has the function of decelerating the effluent gas and making the fine catalyst particles fall back into the reactor. The expander and sampling lines are maintained at 200° C. to avoid the condensation of styrene, non-reacted ethylbenzene and any possible heavy by-products.

The catalytic cycle consists of:
- a reaction phase, in which the ethylbenzene mixed with the inert product or with the paraffin, is fed to the reactor over a period of 10 minutes;
- a stripping phase, into which nitrogen is passed for about 15 minutes to removed the products adsorbed on the catalyst;
- a regeneration phase, into which air is fed for about 45 minutes; and
- a washing phase with nitrogen for about 20 minutes.

The catalytic cycle was carried out continuously for 100 hours without having any loss of activity of the catalyst.

The dehydrogenation reaction is carried out at 560–650° C., whereas the regeneration is carried out at 660° C.

The overall space velocity, expressed as normal liters of ethylbenzene plus normal liters of inert product, is maintained at 300±5 Nl/h/lt of catalytic bed.

During the reaction and stripping phase, the effluent is cooled in a trap immersed in liquid nitrogen in which the non-reacted ethylbenzene, styrene and condensable by-products are condensed. The effluent from the trap is sent to a sack from which hydrogen, inert products and $C_1$–$C_3$, light hydrocarbons from cracking reactions, are recovered.

The liquid fraction is weighed and analyzed by gas-chromatography using an HP 5890 gas chromatograph equipped with a CP WAX 10 capillary column. The dosing of the components is effected using an internal standard.

The gas recovered from the sack is analyzed by gas chromatography using the external standard procedure for the dosing of the components. The contents of the sack are measured with a counter for the material balancing.

The coke deposited on the surface of the catalyst is combusted with air and the effluent collected in a sack. The gas is then analyzed by gas chromatography to dose the concentration of $CO_2$, whereas the volume is measured to establish the quantity of coke formed during the reaction.

The following examples, whose sole purpose is to describe this invention in greater detail, should in no way be considered as limiting the scope of the invention.

EXAMPLE 1

A microspheroidal pseudobohemite to which silica (1.2% by weight) has been added, is prepared, with a particle diameter ranging from 5 to 300μ, by the spray drying of a sol of hydrated alumina and Ludox silica.

A sample of pseudobohemite is calcined at 450° C. for 1 hour and then at 1190° C. for 4 hours in a stream of dry air. The product obtained, consisting of δ, θ and α transition alumina, has a specific surface of 34 m$^2$/g and a porosity of 0.22 cc/g.

150 g of microspheroidal alumina are impregnated, using the "incipient wetness" procedure, with 33 ml of an aqueous solution containing 7.8 g of $KNO_3$ (titer 99.5%) in deionized water, maintained at a temperature of 25° C.

The impregnated product is dried at 80° C. for 1 night and then calcined, in a stream of dry air, at 650° C. for 4 hours in a stream of dry air. The concentration of potassium, expressed as oxide, with respect to the calcined product, is equal to 2.4% by weight.

An impregnating solution is then prepared by dissolving in 23 ml of deionized water: 56.2 g of $Fe(NO_3)_3 \cdot 9H_2O$ (titer 99% by weight) and 6.7 g of $KNO_3$ (titer 99.5% by weight). The solution, heated to 50° C. to complete the dissolution of the salts, is maintained at this temperature for the whole duration of the impregnation.

The alumina modified with potassium oxide (153.6 g) is impregnated with an aliquot (48 g) of impregnating solution, dried at 120° C. for 4 hours and impregnated again with the remaining aliquot of impregnating solution.

The impregnated product is dried at 120° C. for a night and finally calcined at 700° C. for 4 hours.

The weight composition of the formulate is the following: 6.6% $Fe_2O_3$, 4% $K_2O$ and carrier the complement to 100.

The formulate was tested in the dehydrogenation reaction of ethylbenzene to styrene and the average results, after a test run of 100 hours, are indicated in table 1.

EXAMPLE 2

150 g of microspheroidal alumina obtained as described in example 1, are impregnated with a solution containing: 56.3 g of $Fe(NO_3)_3 \cdot 9H_2O$ (titer 99% by weight) and 14.2 g of $KNO_3$ (titer 99.5% by weight).

The impregnation, drying and calcination are carried out with the same procedure described in example 1.

The weight composition of the formulate is the following: 6.6% $Fe_2O_3$, 4% $K_2O$ and carrier the complement to 100.

The dehydrogenation average results of ethylbenzene, after a test run of 100 hours, are indicated in table 1.

EXAMPLE 3

The same procedure is adopted as in example 2, but using an impregnating solution containing: 55.2 g of $Fe(NO_3)_3 \cdot 9H_2O$ (titer 99% by weight) and 6.7 g of $KNO_3$ (titer 99.5% by weight).

The weight composition of the formulate is the following: 6.6% $Fe_2O_3$, 1.9% $K_2O$ and carrier the complement to 100.

The dehydrogenation average results of ethylbenzene, after a test run of 100 hours, are indicated in table 1.

EXAMPLE 4

The same procedure is adopted as in example 2, but using an impregnating solution containing: 53.9 g of $Fe(NO_3)_3 \cdot 9H_2O$ (titer 99% by weight) and 2.8 g of $KNO_3$ (titer 99.5% by weight).

The weight composition of the formulate is the following: 6.5% $Fe_2O_3$, 0.8% $K_2O$ and carrier the complement to 100.

The dehydrogenation average results of ethylbenzene, after a test run of 100 hours, are indicated in table 1.

EXAMPLE 5

The same procedure is adopted as in example 2, but using an impregnating solution containing: 93.1 g of $Fe(NO_3)_3 \cdot 9H_2O$ (titer 99% by weight) and 14. B g of $KNO_3$ (titer 99.5% by weight) and at a temperature of 60° C. The impregnation is carried out in three subsequent steps using 45 g of the mother impregnating solution in each step.

The first aliquot is added on alumina alone which is then dried at 120° C. for 4 hours after impregnation. The dried product is then impregnated with a further 45 g of mother solution and dried at 120° C. This treatment is repeated twice.

The weight composition of the formulate is the following: 10.3% $Fe_2O_3$, 4% $K_2O$ and carrier the complement to 100.

The dehydrogenation average results of ethylbenzene, after a test run of 100 hours, are indicated in table 1.

EXAMPLE 6

A carrier having a surface area of 100 $m^2/g$ has been prepared by calcining the same pseudobohemite containing silica of example 1 at 1060° C.

200 g of such a carrier are impregnated with a solution containing 57.05 g of $Fe(NO_3)_3 \cdot 9H_2O$ (titer 99% b.w.) and 17.23 g of $KNO_3$ (titer 99.5% b.w.), 2.97 g of $Ce(NO_3)_3 \cdot 6H_2O$ and 2.93 g of $La(NO_3)_3 \cdot 6H_2O$ at a temperature of 60° C. The impregnation is carried out in a unique step.

The impregnated material is dried at 120° C. for 4 hours, then calcined at 750° C. for 4 hours.

The weight composition of the formulate is the following: 5.0% $Fe_2O_3$, 3.68% $K_2O$, 0.5% $Ce_2O_3$, 0.5% $La_2O_3$ and carrier the complement to 100.

The dehydrogenation results of ethylbenzene, during a test run of 150 hours, are shown in table 2.

EXAMPLE 7 (COMPARATIVE)

In order to demonstrate the promoting effect of silica in the carrier, a sample has been prepared according to the same procedure of example 6 but based on a carrier, free of silica, having a surface area of 104 $m^2/g$.

The dehydrogenation average results of ethylbenzene, during a test run of 188 hours, are indicated in Table 2.

EXAMPLE 8

The contemporaneous dehydrogenation of ethylbenzene and ethane is carried out in the micro-reactor described above, at a temperature of 600° C., using the catalyst of example 1.

Table 3 enclosed indicates the operating parameters and results obtained.

TABLE 1

| | | | | Feeding | | | KPa | | Conversion | Selectivity | Styrene yield |
|---|---|---|---|---|---|---|---|---|---|---|---|
| Ex. | $Fe_2O_3$ % | $K_2O$ % | T ° C. | EB % vol | $H_2O$ % vol | $N_2$ % vol | P (ata) | pEB | Ethylbenzene % | Styrene mol. % | mol. % |
| 1 | 6.6 | 4 | 540 | 20 | 0 | 80 | (1.1)* | 0.22 | 50 | 93 | 47 |
| 1 bis | 6.6 | 4 | 540 | 20 | 60 | 20 | (1.1)* | 0.22 | 42 | 96 | 40 |
| 1 ter | 6.6 | 4 | 572 | 20 | 60 | 20 | (1.1)* | 0.22 | 53 | 87 | 46 |
| 2 | 6.6 | 4 | 545 | 20 | 0 | 80 | (1.1)* | 0.22 | 50 | 89 | 45 |
| 2 bis | 6.6 | 4 | 570 | 20 | 60 | 20 | (1.1)* | 0.22 | 52 | 85 | 44 |
| 3 | 6.6 | 1.9 | 550 | 20 | 0 | 80 | (1.1)* | 0.22 | 50 | 87 | 44 |
| 3 bis | 6.6 | 1.9 | 580 | 20 | 60 | 20 | (1.1)* | 0.22 | 50 | 84 | 42 |
| 4 | 6.5 | 0.8 | 580 | 20 | 0 | 80 | (1.1)* | 0.22 | 50 | 82 | 41 |
| 4 bis | 6.5 | 0.8 | 580 | 20 | 17 | 63 | (1.1)* | 0.22 | 31 | 79 | 24 |
| 5 | 10.4 | 4 | 550 | 20 | 0 | 80 | (1.1)* | 0.22 | 50 | 87 | 44 |
| 5 bis | 10.4 | 4 | 572 | 20 | 60 | 20 | (1.1)* | 0.22 | 51 | 84 | 43 |

Examples 1 bis–5 bis are comparative examples carried out in the presence of water

*111.63 KPa (abs Pa)

TABLE 2

| | Catalyst composition (%) | | | | | | Feed (% V) | | | | Conv. | Select. Styrene | Yield Styrene |
|---|---|---|---|---|---|---|---|---|---|---|---|---|---|
| Ex. | $Fe_2O_3$ | $K_2O$ | $Ce_2O_3$ | $La_2O_3$ | T ° C. | HOS | EB | $H_2O$ | $N_2$ | P (ata) | EB % | % mol | % mol |
| 6 | 5.0 | 3.6 | 0.5 | 0.5 | 560 | 30 | 20 | 0 | 80 | (1.1)* | 56.2 | 82.7 | 46.5 |
| 6 | | | | | 560 | 150 | 20 | 0 | 80 | (1.1)* | 57.3 | 86.9 | 49.8 |
| 7 | 5.0 | 3.6 | 0.5 | 0.5 | 560 | 34 | 20 | 0 | 80 | (1.1)* | 57.9 | 73.5 | 42.6 |
| 7 | | | | | 580 | 59 | 20 | 0 | 80 | (1.1)* | 64.8 | 56.1 | 36.4 |
| 7 | | | | | 560 | 188 | 20 | 0 | 80 | (1.1)* | 56.9 | 77.9 | 44.3 |

*111.63 KPa (abs Pa)

TABLE 3

| Feeding | | | | | | Conversion | | Selectivity | |
|---|---|---|---|---|---|---|---|---|---|
| EB % vol. | Ethane % vol. | $H_2O$ | Pressure (ata) | PEB | pEthane | EB % | Ethane % | Styrene mol. % | Ethylene mol. % |
| 10 | 90 | 0 | (1.1)* | 0.11 | 0.99 | 59 | 13 | 90 | 90 |
| 20 | 80 | 0 | (1.1)* | 0.22 | 0.88 | 53 | 10 | 92 | 93 |
| 30 | 70 | 0 | (1.1)* | 0.33 | 0.77 | 45 | 8 | 94 | 93 |

*111.63 KPa (abs Pa)

What is claimed is:

1. A process for the dehydrogenation of ethylbenzene to styrene which comprises:
   (a) reacting the ethylbenzene mixed with an inert gas in a fluid-bed reactor, in the presence of a catalytic system consisting of iron oxide and promoters supported on alumina modified with 0.01–10% by weight of silica and operating at a temperature ranging from 400 to 700° C., at a total pressure of 10.13 to 303.9 Kpa (absolute) (0.1 to 3 ata) and with a GHSV space velocity ranging from 50 to 10,000 $h^{-1}$ (normal liters of a mixture of ethylbenzene and inert gas/h×liter of catalyst); and
   (b) regenerating and heating the catalyst in a regenerator at a temperature exceeding 400° C. wherein, the promoter is at least one selected from the group consisting of alkali, alkaline-earth, and lanthanide metal.

2. The process according to claim 1, wherein the catalyst consists of:
   (1) 1–60% by weight of iron oxide;
   (2) 0.1–20% by weight of at least one alkaline or alkaline earth metal oxide;
   (3) 0–15% by weight of a second promoter consisting of at least one rare earth oxide;
   (4) the complement to 100 being a carrier consisting of a microspheroidal alumina selected from those in delta, theta phase or their mixtures, in 10.13 to 303.9 KPa (abs Pa).

3. The process according to claim 1, wherein the catalyst consist of:
   (1) 5–50% by weight of iron oxide;
   (2) 0.5–10% by weight of a metal promoter, expressed as oxide
   (3) the complement to 100 being a carrier consisting of a microspheroidal alumina with a diameter ranging from 50 to 70 microns selected from those in delta, theta phase or their mixtures, in theta+alpha phase or delta+theta+alpha phase modified preferably with 0.08–3% by weight of silica.

4. The process according to claim 1, wherein the promoter is potassium oxide.

5. The process according to claim 1, wherein the promoters are potassium oxide, cerium oxide, lantanium oxide and praseodymium oxide.

6. The process according to claim 1, wherein the catalyst is obtained by:
   (a) addition of an aliquot of the promoter to the support;
   (b) drying at 100–150° C. and, optionally, calcination of the dried support at a temperature not exceeding 900° C.;
   (c) dispersion of the iron oxide and remaining aliquot of promoter onto the support obtained in (a); and
   (d) drying at 100–150° C. and calcination of the dried support at a temperature ranging from 500 to 900° C.;
   and wherein steps c) and d) can be repeated several times.

7. The process according to claim 1, wherein the inert gas is selected from nitrogen, methane, hydrogen and water vapor.

8. The process according to claim 7, wherein the inert gas is selected from nitrogen and methane.

9. The process according to claim 1, wherein the volumetric ratio inert gas/ethylbenzene ranges from 1 to 6.

10. The process according to claim 9, wherein the volumetric ratio ranges from 2 to 4.

11. The process according to claim 1, wherein the dehydrogenation reaction in step (a) is carried out at a temperature ranging from 450 to 650° C., at atmospheric pressure or slightly higher, at a GHSV space velocity ranging from 100 to 1,000 $h^{-1}$ and with a residence time of the catalyst ranging from 5 to 30 minutes.

12. The process according to claim 11, wherein the space velocity ranges from 150 to 300 $h^{-1}$ and the residence time of the catalyst ranges from 10 to 15 minutes.

13. The process according to claim 1, wherein in step (b) the regeneration of the catalyst is carried out with air or oxygen whereas its heating is effected using methane, a fuel gas or by-products of the dehydrogenation reaction, operating at a higher temperature with respect to the average dehydrogenation temperature, at atmospheric pressure or slightly higher, at a space velocity ranging from 100 to 1,000 $h^{-1}$ and with a residence time of the catalyst from 5 to 60 minutes.

14. The process according to claim 1, wherein in step a) the inert gas is a gaseous stream essentially consisting of nitrogen recovered from the combustion products of a regenerator.

15. The process according to claim 1, wherein in step a) the ethylbenzene is fed into the reactor mixed with a paraffin selected from ethane, propane or isobutane obtaining the contemporaneous dehydrogenation of the components of the mixture to give styrene and the corresponding olefins, respectively.

16. The process according to claim 15, wherein the ethylbenzene is fed to the reactor mixed with ethane obtaining the contemporaneous dehydrogenation of the components of the mixture to give styrene and ethylene respectively.

17. The process according to claim 16, wherein the ethylene is recycled to an alkylation unit together with a stream of benzene to give ethylbenzene.

18. The process according to claim 3, wherein the alumina is modified with 0.08–3% by weight if silica.

* * * * *